United States Patent [19]
Wigler et al.

[11] Patent Number: 6,159,713
[45] Date of Patent: Dec. 12, 2000

[54] METHODS FOR PRODUCING PROBES CAPABLE OF DISTINGUISHING DNA FROM RELATED SOURCES

[75] Inventors: Michael Wigler, Lloyd Harbor; Nikolai Lisitsyn, Cold Spring Harbor, both of N.Y.

[73] Assignee: Cold Spring Harbor Laboratory, Cold Spring Harbor, N.Y.

[21] Appl. No.: 09/115,061

[22] Filed: Jul. 14, 1998

Related U.S. Application Data

[63] Continuation of application No. 08/478,242, Jun. 7, 1995, which is a continuation of application No. 08/149,199, Nov. 9, 1993, Pat. No. 5,501,964, which is a continuation-in-part of application No. 07/974,447, Nov. 12, 1992, Pat. No. 5,436,142.

[51] Int. Cl.[7] .............................. C12P 19/34; C12Q 1/68
[52] U.S. Cl. ............................................. 435/91.2; 435/6
[58] Field of Search ........................... 435/6, 91.2, 91.1; 536/22.1, 23.1

[56] References Cited

U.S. PATENT DOCUMENTS 5,436,142   7/1995   Wigler et al. ........................ 435/91.2
5,501,964   3/1996   Wigler et al. ........................ 435/91.2

*Primary Examiner*—Eggerton A. Campbell
*Attorney, Agent, or Firm*—Bertram Rowland; Rae-Venter Law Group P.C.

[57] ABSTRACT

Methodology is provided for developing probes for identifying sequence differences between two related DNA populations, sets of DNA fragments or collections of restriction-endonuclease-cleaved DNA or cDNA. The method employs an initial stage to obtain a representation of both DNA populations, namely using the PCR to produce relatively short fragments, referred to as amplicons. Tester amplicons containing target DNA, sequences of interest, are ligated to adaptors and mixed with excess driver amplicons under melting and annealing conditions, followed by PCR amplification. The process may be repeated so as to greatly enrich the target DNA. Optionally, the target DNA may then be cloned and the DNA used as probes.

2 Claims, 4 Drawing Sheets

RAT LINE SEQUENCE CLONED FROM HUMAN PROSTATE CANCER DNA SAMPLE

```
Human P35    438 GATCTTCCCGGTTGCTGCCGCCACGGAGAGGACTTAGGCAGTATCCCACGAGCAAACTTG 379
                 ||||||||  |||||||||| |||  |||||    |||||| |||  ||||  |||||
Rat L1Rn B6 1042 GATCTTCCTGGTTGCTGCAGCCGCAGAGAGCTCGAGGGCAGCACCCCGAGAGCGAACTTG 1101

Human P35    378 AGCCTTGGAACCACAGGTAGGACCAACTTTTCCCCTGCAAGAAACCCGCCTGGTGAACTC 319
                 |||||  || ||||||||  ||||||||||| ||||||||| ||| | ||||||||||||
Rat L1Rn B6 1102 AGCCTCGGGACCACAGGGAAGACCAACTTTTCTGCTGCAAGTGACCTGTCTGGTGAACTC 1161

Human P35    318 AAGACACAGGCCCACAGGAACAGCTGAAGACCTGTAGAGAGGAAAAACTACATGCCCGAA 259
                 ||||| |||||||||||||||||||||||||||||||||||||||||||||| ||||||
Rat L1Rn B6 1162 AAGACAGAGGCCCACAGGAACAGCTGAAGACCTGTAGAGAGGAAAAACTACACGCCCGAA 1221

Human P35    258 AGCAGAACACTCTGTCCCCATAACTGGCTGAAAGAAAACAGGAAAACAGGTCTACAGCAC 199
                 |||||||||||||||| |||||||| |||||||||||||||||||||||||||||||||
Rat L1Rn B6 1222 AGCAGAACACTCTGTCGCCATAACAGGCTGAAAGAAAACAGGAAAACAGGTCTACAGCAC 1281

Human P35    198 TCCTGACACACAGGCTTATAGGACAGTCTAGCCACGGTCAGAAATAGCAGAACAAAGTAA 139
                 ||||||||||||||||||||| ||||||||||||| ||||||||||||||||||||||
Rat L1Rn B6 1282 TCCTGACACACAGGCTTATAGGGCAGTCTAGCCACTGTCAGAAATAGCAGAACAAAGTAA 1341

Human P35    138 CACTAGAGATAATCTGATGGCGAGAGGCAAGCGCAGGAACCCAAGCAACAGAGACCAAGA 79
                 |||||||||||||||||||| ||||||||||||||||||||||||||||||| ||||||
Rat L1Rn B6 1342 CACTAGAGATAATCTGATGGCAAGAGGCAAGCGCAGGAACCCAAGCAACAGAAACCAAGA 1401

Human P35     78 CTACATGGCATCATCGGAGCCCAATTCTCCCACCAAAATAAACATGGGATATCCAAACAC 19
                 ||||||||| |||||||||||||||||||||||||||| |||||||| ||||||||||
Rat L1Rn B6 1402 CTACATGGCACCATCGGAGCCCAATTCTCCCACCAAAACAAACATGGAATATCCAAACAC 1461

Human P35     18 ACCAGAAAAGCAACATC 2
                 ||||||||||||| |||
Rat L1Rn B6 1462 ACCAGAAAAGCAAGATC 1478
```

Figure 3

RDA of cDNA's:
Tester-mouse brain cDNA containing $10^{-5}$ part of 1.2 kb bacterial gene (Target)

6,159,713

METHODS FOR PRODUCING PROBES CAPABLE OF DISTINGUISHING DNA FROM RELATED SOURCES

This is a continuation of application Ser. No. 08/478,242 filed Jun. 7, 1995, which is a continuation of application Ser. No. 08/149,199 filed Nov. 9, 1993, now U.S. Pat. No. 5,501,964, which is a continuanion-in-part of application Ser. No. 07/974,447, now U.S. Pat. No. 5,436,142.

The U.S. Government has a paid-up license in this invention and the right in limited circumstances to require the patent owner to license others on reasonable terms as provided for by the terms of contract OIG-5R CA39829-08 awarded by the National Institutes of Health.

TECHNICAL FIELD

The field of this invention is DNA analysis.

BACKGROUND

Comparative genomic DNA analysis holds promise for the discovery of sequences which may provide for information concerning polymorphisms, infectious DNA based agents, lesions associated with disease, such as cancer, inherited dominant and recessive traits, and the like. By being able to detect particular DNA sequences which have a function or affect a function of cells, one can monitor pedigrees, so that in breeding animals one can follow the inheritance of particular sequences associated with desirable traits. In humans, there is substantial interest in forensic medicine, diagnostics and genotyping, and determining relationships between various individuals. There is, therefore, substantial interest in providing techniques which allow for the detection of common sequences between sources and sequences which differ between sources.

The mammalian genome is extraordinarily large, having about $6 \times 10^9$ bp. The human genome project has initiated an effort to map and sequence the entire genome. However, much of the early work will be directed more toward determining the site of particular genes, than determining contiguous sequences of a particular chromosome.

Because of the complexity of the human genome, there is a very substantial handling and processing problem with the human genomic DNA. In order to deal with such a large amount of DNA, one must develop processes which allow for simplification and selection, while still providing the desired information. Therefore, efforts must be made which will provide for opportunities which will allow to greater or lesser degrees, dissecting portions of a genome of interest, where comparisons can be made between two different sources of DNA.

Relevant Literature

Efforts at difference analysis at the level of the genome are described by Lamar and Palmer, *Cell* 37, 171 (1984); Kunkel et al., *Proc. Natl. Acad. Sci. USA* 82, 4778 (1985); Nussbaum et al., *Proc. Natl. Acad. Sci. USA* 84, 6521 (1987); Wieland et al., *Proc. Natl. Acad. Sci. USA* 87, 2720 (1990); Straus and Ausubel, *Proc. Natl. Acad. Sci. USA* 87, 1889 (1990).

SUMMARY OF THE INVENTION

Representational difference analysis is provided to determine similarities or differences between two related sources of DNA. In a first step, a representative portion of each genome is prepared, using a restriction endonuclease (RE1), ligation of partially double-stranded adaptors, and the polymerase chain reaction, and cleavage with RE1 to provide a population of relatively small DNA fragments referred to as "amplicons." This stage may be repeated in separate analyses with different restriction endonucleases or different schemes, e.g., fractionation.

The first amplicon of source DNA is referred to as the "driver," which amplicon is used in substantial excess in the subsequent processing of the other, "tester" amplicon. The tester includes the "target" DNA, which DNA is absent in or is present in reduced amounts in driver amplicon. Partially double-stranded PCR adaptors are ligated only to tester amplicon fragments, and the tester and driver DNA combined, melted and reannealed. The termini of the amplicons are filled in and using primers complementary to the adaptors, the DNA mixture is subjected to amplification, wherein the target DNA will undergo exponential amplification and be substantially enriched as compared to driver DNA and non-target tester DNA, which anneals to the driver DNA. Adaptors may then be removed and the cycle repeated using different adaptors. Various modifications may be employed at different stages to further enhance selection of the target DNA.

BRIEF DESCRIPTION OF THE DRAWINGS

FIG. 3 is a sequence comparison of difference product P35 from human prostate cancer (SEQ ID NO:19) with rat retrotransposon RatL1RnB6 (SEQ ID NO:20)

DESCRIPTION OF THE SPECIFIC EMBODIMENTS

Figure 1:
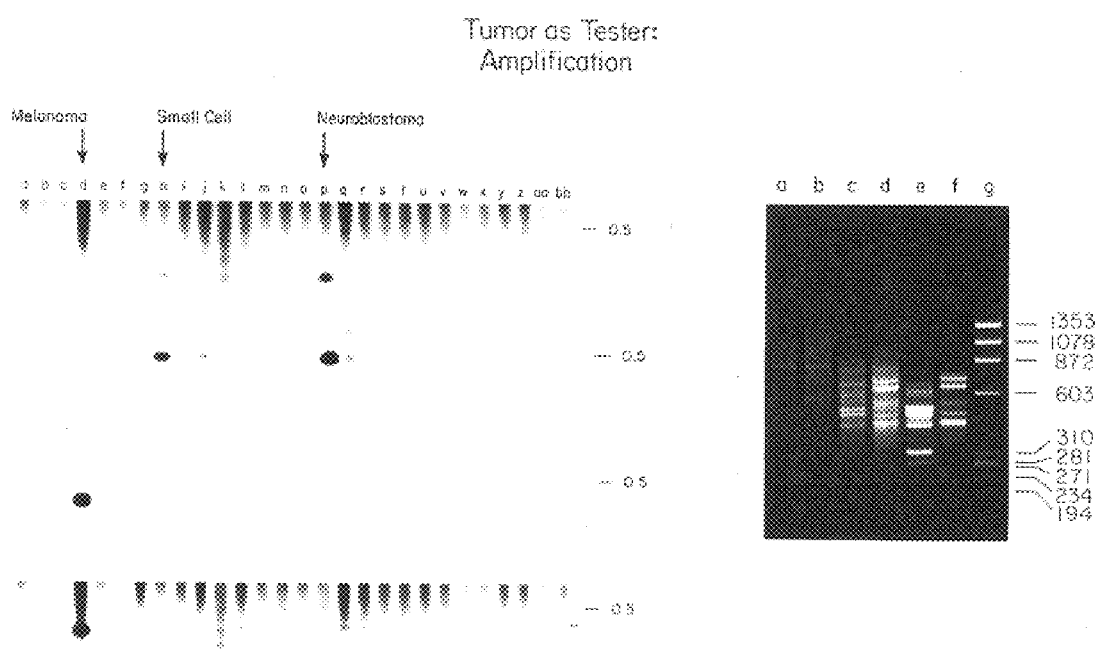
FIG. 1 is a gel electrophoresis and genomic blot analysis of the application of RDA to isolate probes that detect gene amplification.

Methods are provided for representational difference analysis ("RDA") between two sources of DNA. The method permits the detection of sequences which differ between the two sources, where under selective conditions of hybridization, DNA from one of the two sources is not significantly hybridized to DNA from the other source. Sources include genomes, sets of DNA fragments, usually $\geq 0.2$ kbp, collections of restriction endonuclease-cleaved fragments, cDNA or cDNA libraries, etc. The method involves a first step, referred to as representation, and then two or more further steps referred to as subtractive and kinetic enrichment, which may be repeated in order to provide for substantial enrichment of the sequences of interest.

For the purpose of this invention, a number of coined terms will be used. "Driver" DNA is DNA from a source which will be used to determine the presence of DNA in a second source, the "tester" source. Those fragments that are unique or in higher concentration to the tester DNA, as compared to the driver DNA, will be referred to as "target" DNA. The DNA sequences are obtained in a first stage resulting from restriction endonuclease digestion, followed by linkage of adaptors and then amplification with primers complementary to the adaptors. The resulting DNAs are referred to as "amplicons." The amplicons will be characterized by being under about 2 kb and usually at least about 0.5 kb, where the termini will normally have the same restriction endonuclease recognition sequence prior to linkage to the adaptors.

The subject application may find use in a wide variety of situations. In determining the presence or absence of particular DNA sequences, particularly associated with recessive or dominant traits, one can compare two related sources of DNA to determine whether they share the particular sequence, where the sequence may be a coding or non-coding sequence, but will be inherited in association with the DNA sequence(s) associated with the trait. One can use the subject method in forensic medicine, to establish similarities between the DNA from two sources, where one is interested in the degree of relationship between the two sources. The subject method can also be applied in the study of diseases, where one can investigate the presence of a sequence associated with infection, such as a viral sequence which may or may not be integrated into the genome. One may also use the subject methodology in studying changes in the genome as a result of cancer, where cancerous cells may be compared to normal wild-type cells. Thus, the subject methodology has application for detecting genetic rearrangements, genetic loss, gene or other DNA amplification, for identification of DNA from pathogenic organisms integrated into the genome or present in the cellular host, for identification of polymorphisms located at or near genes associated with inherited disorders, for identification of genes which are expressed in a particular cellular host, identification of lesions in neoplastic cells, and the like.

In carrying out the subject method, there are concerns which should be considered when applying the subject method. The PCR may be a source of artefacts, due to the stochastic nature of the process. Therefore, each candidate difference product should be tested for its presence or absence in tester and driver amplicons. Another source of artefact may occur during tissue sampling. Normal flora contaminating a specimen of tester will be readily enriched during difference analysis if that flora is not also present in driver. Genetic mosaicism may be encountered. In situations where one is dealing with polyclonal tissue, such as in a cancer biopsy, there must be a minimum proportion of cells which has the particular mutation in order to be able to detect the presence of the mutation. Therefore, it would be desirable to use cultures of cancer cells or highly purified cancer cells obtained by physical separation as the source for the tester DNA. In the case of discovery of pathogens, there should be a careful matching of the polymorphisms from the infected and uninfected DNA source. In the latter case, tester and/or driver DNA may derive from the same individual, come from an identical twin, come from separate but related individuals, be the pooled DNA from the parents of the tested individual, be pooled DNA from related sources, e.g. cell strains, common genetic dysfunction, or common trait, or the like.

Finally, not all restriction endonucleases will be equivalent in the ease with which target DNA may be identified. Therefore, in each case it will be desirable to use a plurality of restriction endonucleases in separate determinations, not only to ensure that one obtains target DNA within a reasonable number of cycles, but also to increase the number of target DNA sequences that may be obtained.

Turning now to the specific process, the first stage is the isolation of DNA. As already indicated, the DNA may be from any source, eukaryotic or prokaryotic, invertebrate or vertebrate, mammalian or non-mammalian, plant or other higher eukaryotic source. *While, from the standpoint of direct application to human interests, the sources will be human DNA, the subject methodology is applicable to any complex genome, where one is interested in identifying the presence or absence of related DNA, such as laboratory animals, plants, domestic animals, or in any other situation where an inbred or outbred population is of interest. Normally, the DNAs will be from closely-related sources, so that the number of target DNA sequences which are obtained will be relatively restricted in number, frequently being fewer than about $10^4$, usually fewer than about $10^3$, different sequences. While genomic DNA will usually be the source of driver and tester DNA, cDNA may also be used, where one is interested in the differences between two cDNA populations from two different mRNA sources.*

In the first stage, the DNA is isolated, freed of protein, and then substantially completely digested with a restriction endonuclease which provides for relatively infrequent cutting. Usually, the restriction endonuclease will have a consensus sequence of at least six nucleotides and may provide for blunt ends or staggered ends, usually staggered ends. Various restriction endonucleases may be employed, such as BamHI, BglII, HindIII, etc. After digestion of the DNA, double-stranded oligonucleotide adaptors are ligated to the ends of each of the strands of the DNA from the driver and the DNA from the tester. The adaptor will usually be staggered at both ends, with one strand being longer and serving as the sequence complementary to the primer. The adaptor will be double-stranded and have one end complementary to the ends of the dsDNA from the digestion. The DNA from the two sources is then separately amplified, by adding primer and using the polymerase chain reaction with extension for the last round, usually employing at least 10 cycles, more usually at least 15 cycles and generally not more than about 30 cycles, more usually not more than about 25 cycles and preferably about 20 cycles. After this number of cycles, for the most part, the fragments will be mainly less than about 2 kb, usually below about 1.0 kb. The adaptors are then removed by restriction endonuclease digestion and physical separation, using any convenient means.

As distinct from a physical fractionation, the amount of starting material is not limiting when using representation. When employing amplicons of mammalian DNA after cleavage with BamHI, BglII and HindIII, the estimated complexity of the resulting amplicons are 55-fold, 13-fold and 8-fold less than the complexity at the starting genomic DNA, respectively (Bishop et al., *Am. J. Hum. Genet.* 35, 795 [1983]).

Other methods of representing the genome to reduce its complexity may be employed. For example, cleavage with a more frequently cutting enzyme, e.g. a 4 nt consensus sequence restriction enzyme, followed by addition of adaptors, PCR amplification and size fractionation, will achieve this end. Another method might use oligonucleotides as primers to repetitive DNA in the genome to amplify a representational portion of the genome, flanking repetitive sequences.

In the next phase, subtractive and kinetic steps are employed in a single operation of hybridization and amplification. If desired, the steps may be separated, but will preferably be done contemporaneously. The first aspect of this stage is the ligation of PCR adaptors to the 5' ends of tester amplicon fragments or the products of previous rounds of enrichment, when the procedure is reiterated. Ligation to the 3' ends of tester amplicon is to be avoided, which can be achieved, for example, by using adaptors that are not phosphorylated at their 5' ends. Usually, the adaptor chain complementary to the primer will be at least about 12 nt, more usually at least 17 nt, and generally fewer than about 200 nt, more usually fewer than about 100 nt. Any convenient method for ligation of the adaptors to the 5' ends may be employed, as appropriate.

The tester amplicon fragments joined to the adaptors are then combined with the driver amplicon fragments and melted and allowed to reanneal. The driver amplicon fragments will be present in substantial excess, usually at least 5-fold excess, and the excess may exceed 50 or more, usually not exceeding about $10^8$-fold excess, more usually not exceeding 500-fold excess. The ratio of driver DNA to tester DNA need not be constant for the different rounds. Usually, the ratio will increase with successive rounds where the increase may vary from about 1:1 to $10^3$. The initial ratio will generally be in the range of about 10 to 1000-fold excess. Conveniently, melting will be achieved by heating at an elevated temperature, generally $\geq 95°$ C. and hybridization proceeding at about 60° C., where various buffers may be employed, as well as salt concentrations, to provide the necessary stringency. Usually, fairly high stringencies will be employed, generally at least about equivalent to or greater than about 0.1 M NaCl, usually about 1 M NaCl.

After melting and reannealing, there will be a substantial enrichment of target DNA in the total double-stranded DNA, since the target DNA will not be inhibited from self-annealing due to the lack or relative deficiency of complementary sequences present in the driver DNA.

Overhangs are then filled in by employing any convenient DNA polymerase, e.g., Taq DNA polymerase, in the presence of the four nucleotides, whereby only double-stranded, self-reannealed tester DNA will have filled-in adaptors at each end of the amplicon. Since the driver DNA does not inhibit target DNA from self-annealing, while the driver DNA inhibits non-target tester DNA from self-annealing, there is a substantial enrichment in the target DNA as compared to the total tester DNA.

The double-stranded self-reannealed tester amplicon will then be amplified under conventional polymerase chain reaction conditions, usually involving at least about 5 cycles, frequently as many as 10 cycles and usually not more than about 40 cycles, preferably not more than about 30 cycles. The amplification may be interrupted about midway and single-stranded DNA degraded using an appropriate nuclease. Various nucleases may be employed, particularly mung bean nuclease.

The resulting double-stranded DNA mixture may then be digested with a restriction endonuclease which removes the adaptors from the tester DNA. The tester DNA may be separated from the adaptor sequence, using any convenient means which permits separation by size. Gel filtration or gel electrophoresis may be conveniently employed. The amplicons may then be ligated to a second set of adaptors, usually different from the first or previous set and the cycle of melting in the presence of excess driver amplicon, annealing, filling in overhangs, and PCR amplification repeated. Later cycles may rely on the previous adaptors. In the subject process, this cycle may be repeated one or more times, there usually being at least 2 rounds or repetitions and not more than about 6 rounds, usually 2 to 4 rounds being sufficient.

It will frequently be of interest to carry out the process more than once, where different restriction endonucleases are employed for each study. In this way, different amplicons will be obtained and one may obtain different information. Depending upon the purpose for the process, two or more restriction endonucleases may be utilized in separate preparations of the amplicons. One may also compare the probes obtained with different restriction endonucleases to determine if they overlap, bind to genomic DNA sequences which are proximal, are part of the same gene or polymorphic region, and the like.

In carrying out the process, the first round is mainly subtractive. Subsequent rounds have a greatly-increased component of kinetic enrichment. For example, if target DNA is equimolar with respect to tester DNA (i.e. a single copy), and if driver amplicon is taken in N-fold excess to tester amplicon, assuming virtually complete reannealing of driver amplicon, target will be enriched N times after the first round. After the second round, target will be enriched $N^2$ multiplied by a factor due to the subtractive component, and after the third time, at least the square of that. If N is 50, at the end of the second round, target will be enriched by about $10^4$, and at the end of the third round, on the order of $10^8$. In general a single cycle of subtraction can be expected to yield enrichments of target in the order of fN, where N is the molar excess of driver amplicon to tester amplicon and f is the fraction of driver amplicon that reanneals.

The resulting target DNA or difference product may be further enriched for probes defining differences between the DNA sources. Conveniently, the sequences may be cloned and then screened using Southern blots or other technique for determining complementation against tester and driver amplicons. Those clones which hybridize to tester amplicons and not driver amplicons may then be used further.

The resulting target DNA may be used as probes to identify sites on the tester DNA genome which differ from the driver DNA. For this purpose, they may be labeled in a variety of ways, such as with radioactive labels, biotin, fluorescers, etc. Desirably, in order to obtain substantially homogeneous compositions of each of the target amplicons, the target amplicons may be cloned by inserting into an appropriate cloning vector for cloning in a prokaryotic host. If desired, the cloned DNA may be sequenced to determine the nature of the target DNA. Alternatively, the cloned DNA may be labeled as described above, and used as probes to identify fragments in libraries carrying the target DNA. The target DNA may be used to identify the differences which may be present between the two sources of DNA.

Where a plurality of probes for target DNA are obtained, they may be referred to as putative probes until established as true probes. Conveniently, the sequences may be cloned and then screened using Southern blots or other technique for determining complementation against tester and driver amplicons. Thus, the group of probes may include hybridizing sequences which hybridize to both driver and tester DNA. One can quickly determine those putative probes which do not distinguish between driver and tester DNA by hybridizing, e.g. Southern hybridizidng, the probe to driver and tester amplicons. Where the putative probe binds to both driver and tester amplicons, the probe may be discarded. Those clones which hybridize to tester amplicons and not driver amplicons may then be used further. This screen is particularly useful where at least 5, more usually at least 10 putative probes are obtained.

In pedigree analysis, the subject process may be used to define sequences which are present in one member of a family and not present in another. In this way, one may then compare other members of the family as to whether they carry the same DNA or it is absent. This may find use in forensic medicine, where there may be an interest in the relationship between two individuals, a sample obtained from a source and an individual, or the like.

The subject method can also be used to construct libraries of probes for genetic polymorphisms, which may be referred to as PARFs, which is operationally defined as a polymorphic restriction endonuclease fragment, present in the amplified DNA from one genome and not present in the amplified DNA from a different genome from a like organism. For example, if one of two BamHI sites flanking a short BamHI fragment in tester DNA is absent in both alleles from driver DNA, leading to only large BamHI fragments in driver, the short BamHI fragment of tester will be present in its BamHI amplicon, but absent in the BamHI amplicon of the driver. Thus, the restriction fragment would directly lead to a probe which will distinguish between the two genomes.

It should be appreciated, that where the amplicons are cloned, there may be substantial redundancy in individually-picked clones. Therefore, the efficiency of selecting different probes will vary substantially depending upon the frequency in which the amplicon was present in the mixture prior to cloning, which may be as a result of the varied efficiency of amplification, or other artefacts which are built into the methodology.

The subject method can be used to isolate probes for pathogens, where DNA which is suspected of being infected may be compared to DNA which is believed to be uninfected. For example, if one were interested in a virus which is tropic for a particular cell type or tissue, e.g., HIV for T-cells and macrophages or hepatitis B virus for liver, one could take tissue from the source suspected of infection for which the virus is tropic and tissue from another site in the same individual, where such virus should not be present. By carrying out the process, one should obtain probes which would be specific for the virus, since by appropriate selection of the sources of the cells, one would not anticipate any other differences.

A limitation of the subject process, which will be applicable to viruses, as well as other situations, is that the population carrying the target DNA should be a reasonable proportion of the total number of cells from which the tester DNA is derived. As indicated above, where one is interested in the presence of integrated pathogenic DNA, it may be that only a small proportion of these cells in the tissue are infected. It may, therefore, be desirable to normalize the tester sequences, in order to equalize the concentrations of all tester sequences, prior to the subtractive and kinetic enrichment (Patanjali et al., *Proc. Natl. Acad. Sci. USA* 88, 1943 [1991]).

Application of RDA to the discovery of pathogens desirably requires a careful matching of the polymorphisms from the infected and uninfected DNA sources. Tester and driver DNA can derive from the same individual, if the individual is not a genetic mosaic. These DNAs should not derive from unrelated individuals, as the abundant polymorphic differences in their DNAs would obscure the detection of the pathogen. However, the uninfected DNA source (driver) could, in principle, come from an identical twin, or be the pooled DNA from the parents of the infected individual, because virtually all of the DNA restriction fragments found in the genomic DNA of the infected individual can be expected to be present in at least one parent DNA.

The subject methodology may also be applied to detecting genomic alterations occurring in cancer cells. These could be of three distinct types: those that result in loss of restriction endonuclease fragments, such as might occur from deletions or gene conversions extending over heterozygous polymorphisms; those that produce new restriction endonuclease fragments, such as might result from point mutations or genomic rearrangements; and those that result in the amplification of DNA, usually incorportating a gene. In the second and third cases, RDA could be applied without modifications using DNA from cancer cells as tester and normal DNA as driver. However, the presence of normal stroma in a cancer biopsy could interfere with the detection of loss of genetic information in the cancer cell. Hence, either cultures of cancer cells or highly-purified cancer cells obtained by physical separation would be needed as the source for tester in the first case.

These restraints do not apply to the detection of genomic rearrangements. Genomic rearrangements, including translocations, insertions, inversions and deletions, will result in the creation of new restriction endonuclease fragments bridging the site of the rearrangement. Some of these bridging fragments may be amplifiable, while at least one of the fragments from which they derive in normal DNA is not. Such bridging fragments would be discoverable by RDA, when DNA from the tumor is used for preparation of tester amplicons and DNA from normal tissue of the same individual is used for preparation of driver amplicons.

The different-sized restriction endonuclease fragments created by genomic rearrangements may be exploited another way. Fractionated size classes from tumor DNA digests will sometimes contain sequences that are not present in comparable-size classes from normal DNA. Using the former as tester and the latter as driver, one can prepare amplicons after cleavage with a second restriction endonuclease and compare these by RDA in order to clone amplifiable restriction endonuclease fragments in proximity to the point of genetic rearrangement. With either of the above-indicated methods, the presence of normal cells among the tumor cells will not obscure the detection of probes for the rearrangement.

In the final situation, DNA amplification, it appears that the detection of amplification is a result of kinetic enrichment during RDA. Being able to detect amplified sequences can find application in cancer prognosis, since it has been found that amplification of oncogenes indicates a poor prognosis.

When RDA is applied to different individuals, it will yield a collection of polymorphisms of a type, which has been previously referred to as PARFs. Thus, RDA can be used for generating new sets of polymorphisms, not only for species that have not previously undergone extensive molecular genetic characterization, but also for well-studied species as humans and mice. Since PARFs most often detect binary polymorphisms, they can serve as a panel of probes that can be used with a standardized format for genetic typing.

In yet another application, RDA can yield probes for PARFs present in the DNA of an individual from a founder group affected by some autosomal dominant inherited disorder (the tester), but absent in the DNA of an individual from a normal group (the driver). Conversely, RDA can yield probes for PARFs present in the DNA of a normal individual (the tester), but absent in the DNA of an individual from the founder group affected by a recessive inherited disorder (the driver). Combined with methodologies for coincidence cloning (Brooks and Porteous, *Nuc. Acid Res.* 19, 2609 [1991]), such applications can accelerate the discovery of probes for rare PARFs in linkage disequilibrium with the dominant locus, or the absence of common PARFs in linkage disequilibrium with the recessive locus.

In many laboratory animals and plants there are congenic strains, where a particular gene has been transferred from one genetic background onto another by successive generations of backcrossing. Such strains will be genetically identical except in a relatively small region surrounding the gene of interest. The region will be typically small enough to permit chromosomal walking to the target gene, but large enough for the needs of the subject methodology.

The subject methodology may be applied to the discovery of polymorphisms that are genetically linked to an inherited trait such as a disease susceptibility or a behavorial abnormality. To utilize the subject methodology for this purpose, it is desirable to use pools of DNAs from a group of individual for use as either tester, driver or both. When used this way, the method may yield probes that detect polymorphic alleles that are present in one group and not in another. In particular, when such pools are used as driver, the probes obtained for restriction endonuclease polymorphisms ("PARFs") that distinguish tester from all individuals in the driver pool. When pools are used as tester, the method yields PARFs that distinguish at least one member of the tester pool from the driver individual. In the most challenging example, when both tester and driver are pooled DNAs from groups of individuals, the method yields PARFs that distinguish at least one member of the tester group from all members of the driver group.

Pooling may be demonstrated in a variety of situations. One application uses transmission genetics to produce a collection of siblings with the property that their pooled DNA is homozygous in the region of a target gene but heterozygous elsewhere in the genome. As an illustration, if two inbred strains differ at a target locus L of interest, one strain A carries a recessive allele ($a^-$) and the other strain B carries a dominant allele ($a^+$), for tester one can use strain B, while for Driver, one performs an F2 intercross between the strains, selects k progeny showing the recessive phenotype, and mixes their DNA together. When employing the subject method, B alleles should be subtracted everywhere in the genome except in a region around L.

The targetting of the method can be further improved where the locus L has been genetically mapped between two flanking genetic markers, X and Y. For the driver, one can select ½ k progeny in which a crossover had occurred between X and L and ½ k progeny in which a crossover had occurred between L and Y. this would guarantee that the proportion of B alleles is 25% at X and Y. This ensures that the region over which the proportion of B alleles is very low is restricted to the interval X-Y.

The pools may be of various sizes depending on the source of DNA. From large genomes, such as mammalian and plant genomes, generally a pool as small as 8 different sources may be employed, usually 10, and generally not more than 50, usually not more than about 20.

Other applications may involve spontaneous germ line genomic rearrangements. The genome of such an infected individual will include restriction endonuclease fragments that are present in neither parent. This situation is analogous to genetic rearrangements occurring in cancer cells, which has been previously discussed.

To ensure that the subject process has operated properly, it will normally be desirable to test candidate difference products (target DNA) for its presence or absence in tester and driver amplicons. Also of concern will be the presence of flora, which may contaminate tester, but is not present in driver. Genetic mosaicism will also interfere with the subject methodology. However, in a wide variety of contexts, the subject method will efficiently provide sequences which can be used for analyzing differences between two genomes as a result of a wide variety of events.

The following examples are offered by way of illustration and not by way of limitation.

EXPERIMENTAL

Preparation of Amplicons.

10 μg of high molecular weight DNA purified from the lymphoid cell line DRL 484 (a gift of T. Caskey, Baylor College) was used for preparation of driver amplicons and 10 μg of the same DNA, containing equimolar amounts of target (120 pg of adenovirus-2 DNA and/or 160 pg of λ phage DNA, both from New England Biolabs) was taken for preparation of tester amplicons. Both tester and driver DNA samples were digested with restriction endonuclease (New England Biolabs) and 1 μg of each DNA digest was mixed with 0.5 nmoles of 24-mer and of 12-mer unphosphorylated oligonucleotides (set 1, see Table 1) in 30 μL of T4 DNA ligase buffer (New England Biolabs).

TABLE 1

Sequences of Primers Used for Representational Difference Analysis.

| Primer Set | Name | | Sequence |
|---|---|---|---|
| 1 | R Bgl10 | (SEQ ID NO:1) | 5'-AGCACTCTCCAGCCTCTCACCGCA-3' |
|   | R Bgl12 | (SEQ ID NO:2) | 5'-GATCTGCGGTGA-3' |
| 2 | J Bgl24 | (SEQ ID NO:3) | 5'-ACCGACGTCGACTATCCATGAACA-3' |
|   | J Bgl12 | (SEQ ID NO:4) | 5'-GATCTGTTCATG-3' |
| 3 | N BgL24 | (SEQ ID NO:5) | 5'-AGGCAACTGTGCTATCCGAGGGAA-3' |
|   | N Bgl12 | (SEQ ID NO:6) | 5'-GATCTTCCCTCG-3' |
| 1 | R Bam24 | (SEQ ID NO:7) | 5'-AGCACTCTCCAGCCTCTCACCGAG-3' |
| 2 | J Bam24 | (SEQ ID NO:9) | 5'-ACCGACGTCGACTATCCATGAACG-3' |
|   | J Bam12 | (SEQ ID NO:10) | 5'-GATCCGTTCATG-3' |
| 3 | N Bam24 | (SEQ ID NO:11) | 5'-AGGCAACTGTGCTATCCGAGGGAG-3' |
|   | N Bam12 | (SEQ ID NO:12) | 5'-GATCCTCCCTCG-3' |

TABLE 1-continued

Sequences of Primers Used for Representational Difference Analysis.

| Primer Set | Name | Sequence |
|---|---|---|
| 1 | R Hind24 | Same as J Bgl24 (see above) |
|  | R Hind12 (SEQ ID NO:13) | 5'-AGCTTGCGGTGA-3' |
| 2 | J Hind24 | Same as J Bgl24 (see above) |
|  | J Hind12 (SEQ ID NO:14) | 5'-AGCTTGTTCATG-3' |
| 3 | N Hind24 (SEQ ID NO:15) | 5'-AGGCAGCTGTGGTATCGAGGGAGA-3' |
|  | N Hind12 (SEQ ID NO:16) | 5'-AGCTTCTCCCTC-3' |
| 1 | Seq24 (SEQ ID NO:17) | 5'-CGACGTTGTAAAACGACGGCCAGT-3 |
|  | Rev25 (SEQ ID NO:18) | 5'-CACACAGGAAACAGCTATGACCATG-3' |

Primer set 1 (R series) is used for representations, and sets 2 (j series) and 3 (N series) are used for odd and even hybridization/amplifications, respectively. Oligonucleotide design was checked for the absence of strong secondary structure using the OLIGO computer program (National Biosciences).

Oligonucleotides were annealed by cooling the mixture gradually from 50° C. to 10° C. for one hour and then ligated to human DNA fragments by overnight incubation with 400 U of T4 DNA ligase at 16° C. Following ligation, both tester and driver DNA samples were amplified. Each of 10 tubes taken for preparation of driver amplicons and 2 tubes used for preparation of tester amplicons contained in a volume of 400 μl: 67 mM Tris-HCl, pH 8.8 at 25° C., 4 mM MgCl$_2$, 16 mM (NH$_4$)$_2$SO$_4$, 10 mM β-mercaptoethanol, 100 μg/ml bovine serum albumin, 200 μM (each) dATP, dGTP, dCTP, and dTTP, 1 μM 24-mer primer and 80 ng of DNA with ligated adaptors. The tubes were incubated for 3 min. at 72° C. in a thermal cycler (Perkin Elmer Cetus), 15 U of Taq polymerase (AmpliTaq, Perkin Elmer Cetus) was added, the reactions were overlaid with mineral oil, incubated for 5 min. to fill in 5' protruding ends of ligated adaptors, and amplified for 20 cycles (each cycle including 1 min. incubation at 95° C. and 3 min. at 72° C., with the last cycle followed by an extension at 72° C. for 10 min.). After amplification both driver and tester amplicons were digested with the same restriction endonuclease (10 U/μg) to cleave away adaptors. 10 μg of tester amplicon DNA digest was electrophoresed through 2% NuSieve agarose (low melting point, FMC Bio Products), and DNA fragments (150–1500 bp) were recovered after melting of the agarose slice and Qiagen-tip20 chromatography (Quiagen Inc.) to remove adaptors. These fragments were ligated to a new set of adaptors (primer set 2, see Table 1) in preparation for the first round of hybridization and amplification.

DNA Hybridization and Amplification Step.

0.5 μg of the tester amplicon ligated to adaptors and 40 μg of driver amplicon DNA were mixed, ethanol precipitated, dissolved in 4 μl of 3×EE buffer (Straus and Ausbel, Proc. Natl. Acad. Sci. USA 87, 1889 [1990]) and overlaid with 30 μl of mineral oil (Perkin Elmer Cetus). Following heat denaturation 1 μl of 5 M NaCl solution was added and DNA was hybridized for 20 h at 67° C. At the end of hybridization, ¹/₁₀th part of the resulting DNA was incubated with 15 U of Taq polymerase (5 min., 72° C.) in 400 μl of PCR mixture without primer to fill in ends of reannealed tester, and then amplified for 10 cycles (1 min. at 95° C., 3 min. at 70° C., followed by 10 min. extension for the last round) after addition of the same 24-mer oligonucleotide to which tester was ligated. Single stranded DNA molecules present after amplification were degraded by 30 min. incubation with 20 U of mung bean nuclease (New England Biolabs) in a volume of 40 μl as recommended by the supplier followed by 5-fold dilution of the sample in 50 mM Tris-HCl, pH 8.9 and heat inactivation of enzyme (95° C., 5 min.). 40 μl of the solution was amplified for 15–20 cycles under the same conditions as before the mung bean nuclease treatment. Amplified DNA (3–5 μg) was digested with the original restriction endonuclease and 200 ng of the digest was ligated to the third adaptor set (see Table 1). 50–100 ng of this DNA was mixed with 40 μg of driver amplicon and the hybridization and amplification procedures were repeated as in the first cycle. 200 ng of the digest obtained after the second hybridization/amplification step was then ligated to the second set of adaptors and 100–400 pg of this material together with 40 μg of driver amplicon was taken for the third round of hybridization, with the final amplification after mung bean nuclease digestion for 20–25 cycles. A fourth hybridization/amplification step was performed after taking 5 pg of material from the third round ligated to adaptors of the third set and mixing it with 40 μg of driver amplicon.

EXAMPLE 1

Representational Difference Analysis with Viral DNAs Added as Targets.

Single-copy levels of adenovirus and/or bacteriophage λ DNA was added to human DNA to create a model tester, and used with the same human DNA without viral DNA as driver. BglII amplicons from human DNA with adenovirus and λ DNAs as targets or HindIII amplicons with λ DNA as target were prepared. With BglII amplicons, small λ and adenovirus fragments were the major difference products, even after two rounds, as evidenced by agarose gel electrophoresis. This represented an enrichment of >5×10$^6$-fold from the starting material and a probable enrichment of about 4×10$^5$-fold from amplicons.

The enrichment from HindIII amplicons was not as effective. The λ HindIII fragment was greatly enriched after the third round as evidenced by blot hybridization, but still not to homogeneity. After the fourth round the expected target fragment was purified to near homogeneity. The difference between the experience with the HindIII restriction endonuclease and the BglII restriction endonuclease may be related to the greater sequence complexity of the HindIII amplicons. When the complexity of the driver is too high, subtractive and kinetic enrichments are diminished and competing processes may dominate. The competing processes may involve the emergence of efficiently-amplified repetitive sequences in tester.

EXAMPLE 2

Representational Difference Analysis of DNAs from Two Individuals.

Driver and tester amplicons were prepared from human lymphoblastoid cell cultures GM05901 and GM05987, respectively (Amish Pedigree 884, Human Genetic Mutant Cell Repository, Camden, N.J.). Amplicons were prepared after cleavage with BamHI, BglII or HindIII. Difference products between amplicons were obtained as described above and size fractionated by gel electrophoresis. A discrete but complex pattern of bands was observed in each case. After three hybridizations/amplifications, difference products were cloned into plasmids. For each difference product, three probes were picked for blot hybridization analysis. It was found that all of them were polymorphic within the Amish family data. BamHI difference products were analyzed in greatest detail.

Each of the BamHI probes derived from the above experiment was also used in blot hybridizations to amplicons from the family and 10 other unrelated human DNAs extracted from cell lines or placentas (Table 2). Complete concordance between this method and Southern blotting of total genomic DNA was found. These results support the conclusion that the probes which detect polymorphisms within the Amish family will also detect polymorphisms in the human population at large. As indicated previously, these polymorphisms are referred to as PARFs (polymorphic amplifiable restriction endonuclease fragments).

The probes for PARFs are not equally abundant in the difference product. To obtain a measure of this unevenness, each cloned BamHI PARF was hybridized to a grid of 90 individually randomly-picked clones from the difference product of the two siblings, and its frequency in the collection was determined (see percent value in Table 2). From a total of 90 randomly-picked elements, only 20 distinct polymorphic probes were present.

It should be noted that the protocol was designed for the detection of a small number of differences between two nearly-identical genomes. Where probes for polymorphic loci are deliberately sought, more representative difference

TABLE 2

Screening for Presence of BamHI PARFs in 17 Human DNA Samples.

| Probe Number (%) | A | B | C | D | E | F | G | H | I | J | K | L | M | N | O | P | Q | Length of alleles in kbp |  |
|---|---|---|---|---|---|---|---|---|---|---|---|---|---|---|---|---|---|---|---|
|  |  |  |  |  |  |  |  |  |  |  |  |  |  |  |  |  |  | Large | Small |
| 1 (15.5) | − | + | − | + | + | + | + | + | + | + | + | + | + | + | + | + | + | 15 | 0.61, 0.67[a] |
| 11 (14.4) | − | + | − | − | + | + | − | − | − | − | − | − | − | − | − | − | − | 15 | 0.6 |
| 6 (8.9) | − | + | + | + | + | + | + | + | + | + | + | − | + | − | + | − | + | 3.5 | 0.58 |
| 19 (5.5) | − | + | + | − | + | + | + | + | + | + | − | + | − | − | + | + | + | 15 | 0.51 |
| 17 (4.4) | − | + | − | − | + | + | + | + | + | − | − | − | − | − | − | − | + | 8 | 0.48 |
| 22 (4.4) | − | + | + | + | − | + | + | + | − | + | + | + | + | − | + | + | + | 6.5 | 0.67 |
| 8 (3.3) | − | + | + | + | − | + | + | + | + | + | − | − | − | + | + | + | + | ND | 0.62 |
| 24 (3.3) | − | + | − | + | + | + | + | + | − | + | + | − | + | + | − | + | − | >50 | 0.65 |
| 26 (3.3) | − | + | + | − | − | − | + | + | + | + | − | + | − | + | + | + | − | 6, 5[b] | 0.65 |
| 9 (2.2) | − | + | − | − | − | − | + | − | + | − | − | − | − | − | − | − | − | ND | 0.47 |
| 65 (2.2) | − | + | + | + | + | + | + | + | + | + | + | + | − | + | + | − | + | 4 | 0.74 |
| 3 (1.1) | − | + | + | + | − | + | + | + | + | + | + | − | + | − | + | + | + | ND | 0.5 |

BamHI amplicons were prepared from DNA from seven Amish pedigree lymphoblastoid cell cultures, GM05901 (driver), GM05987 (tester), GM05918, GM05961, GM05963, GM05993, GM05995 (columns A–G), five different placentas (columns H–L), three lymphoblastoid cell lines established from the biopsies of leukemic patients (columns M, N, O) and two fibroblast cell cultures, DRL 484, and DRL 569 (a gift of T. Caskey, Baylor College) established from the biopsies of DMD patients (columns P, Q), transferred to GenScreen membrane, and hybridized to the indicated probes. "%" indicates the percent of clones in a BamHI PARF collection of difference products cloned after three hybridization-amplification steps that hybridized to the indicated clone. "+" means that the small BamHI PARF allele was present in the sample (i.e. the probe hybridized to a band of the correct size in the amplicon); "−" means that the small allele was not detected. See FIG. 3C for a sample of the actual data. The lengths of the alleles hybridizing to PARFs are indicated, where known. "ND" means not determined.
[a]Two different small alleles were found in the human population.
[b]Two different large alleles were found in the human population.

Of 20 randomly-picked clones, 12 unique clones remained after removing redundancies, and the inserts from 9 of these were used as probes in Southern blots of tester, driver and 5 other members of the family (GM05918, GM05987 [tester], GM05901 [driver], GM05961, GM05963, GM05993, and GM05995 from Amish pedigree 884). All probes detected small BamHI fragments in the tester (Table 2, col. B) and only large BamHI fragments in the driver (Table 2, col. A). The blot hybridization pattern for each probe was completely consistent with a Mendelian pattern of inheritance. The results demonstrate that collec- products can be generated by diminishing the number of rounds of hybridization/amplification, increasing the complexity of the representation and/or decreasing the total number of PCR cycles.

***The following is an exemplary protocol used in the following examples, except where otherwise indicated.

DIFFERENCE ANALYSIS PROTOCOL

I. Preparation of Amplicons
  1. Restriction of DNA.
    a. Digest 10 μg of Driver and Tester DNA with a restriction enzyme chosen for representation, taking 10 U/μg of high molecular weight DNA.

b. Extract with equal volumes of phenol and phenol/chloroform.

c. Add NaOAc to final concentration 0.3 M, EtOH ppt., wash with 70% EtOH, dry in vacuo and resuspend at 0.1 mg/ml.

2. Purification of oligonucleotides a. Attach Sep-Paq cartridge (Waters, Millipore) to 5 ml syringe and wash it with 10 ml of acetonitrile and 10 ml of water.

b. Load 20 $OD_{260}$ of the oligonucleotide in 2 ml of water, wash with 10 ml of water and elute with 60% MeOH, collecting 7 fractions in Eppendorf tubes (3 drops per each tube).

c. Measure DNA concentration of 200 fold dilutions at $\lambda$=260 nm, combine DNA containing fractions (approx. 500 $\mu$l) and concentrate by liophylization up to 200–300 $\mu$l.

d. EtOH ppt. (use 4 vol. of EtOH) after addition of 1/10 vol. 3 M NaOAc, wash with 100% EtOH, dry, resuspend at 62 pmol/$\mu$l (12 $OD_{260}$/ml for 24-mers and 6 $OD_{260}$/ml for 12-mers).

3. Ligation of adaptors a. Mix: 20 $\mu$l (2 $\mu$g) of Driver or Tester DNA digest, 15 $\mu$l of each 12-mer and 24-mer (primer set 1), 4 $\mu$l of dd$H_2O$, 6 $\mu$l of 10xLigase buffer.

b. To anneal the oligonucleotides, place the tubes in a heating block (Termoline DriBath, holes filled with glycerol) at 50–55° C. and then place the block in a cold room for approx. 1 h, until the temperature will decrease to 10–15° C.

c. Place the tubes on ice for 3 min., add 2 $\mu$l (400 U/$\mu$l) of T4 DNA ligase, and incubate overnight at 12–16° C.

4. PCR a. Add 940 $\mu$l of TE(10 mM Tris-HCl, pH 8.0/1 mM EDTA) plus tRNA (20 $\mu$g/ml) buffer to each ligate to make a dilution.

b. Makes 2 tubes of PCR mix for preparation of Tester amplicon and 10 tubes for preparation of Driver amplicon, each containing:
80 $\mu$l of 5xPCR buffer (335 mM Tris-HCl, pH 8.8 at 25° C., 20 mM MgCl$_2$, 80 mM (NH$_4$)$_2$SO$_4$, 50 mM β-mercaptoethanol, 0.5 mg/ml of bovine serum albumin)
32 $\mu$l of chase solution (4 mM of each dATP, dGTP, dCTP, dTTP)
8 $\mu$l of 24-mer oligonucleotide (primer set 1)
240 $\mu$l of dd$H_2O$.

c. Add 40 $\mu$l of DNA ligate dilution (80 ng) in each tube and place the tubes in a Thermocycler (Perkin Elmer Cetus) at 72° C.

d. To fill-in 5'-protruding ends of the ligated adaptors, add 3 $\mu$l (15 U) of AmpliTaq DNA polymerase in each tube (use Aerosol Barrier Pipet Tips), mix, overlay with 110 $\mu$l of mineral oil and incubate for 5 min.

e. Amplify for 20 cycles (1 min. at 95° C. and 3 min. at 72° C.) with the last cycle followed by extension at 72° C. for 10 min.

5. Restriction of amplicons a. Remove mineral oil, combine the contents of each of 2 PCR tubes in Eppendorf, extract with 600 $\mu$l of phenol and phenol/chloroform.

b. Add 1/10 vol. of 3 M NaOAc and equal volume of isopropanol, incubate for 15 min. in ice bath, spin, wash, dry. Resuspend Driver and Tester amplicons in TE at concentration 0.2–0.4 mg/ml (expecting 10–20 $\mu$g of DNA amplicon from one PCR tube), check DNA concentration using EtdBr solution (2 $\mu$g/ml).

c. Digest both Driver DNA (200 $\mu$g) and Tester DNA (20 $\mu$g) with initially chosen restriction endonuclease in order to cleave the adaptors, extract and iProOH ppt. as above.

d. Resuspend Driver amplicon DNA digest in TE at approx. 1 mg/ml and Tester amplicon DNA digest at 0.2–0.4 mg/ml. Measure Driver and Tester DNA concentrations by EtdBr fluorescence and agarose gel electrophoresis. Adjust Driver DNA concentration to 0.5 mg/ml and Tester DNA concentration to 0.1 mg/ml.

6. Change of adaptors on Tester amplicon a. Load 10 $\mu$g of Tester amplicon DNA digest on 2% NuSieve agarose gel (low melting point, FMC Bioproducts).

b. Cut agarose slice (0.2–0.4 g) containing fragments 150–1500 bp in length and put it in a 5 ml Falcon tube. Add 0.4 ml of 0.5 M MOPS pH 7.0, 0.4 ml 5 M NaCl and 3 ml of dd$H_2O$.

c. Mix, melt at 72° C. in a heating block for 10 min., repeat this step one more time.

d. Pass warm solution (30–50° C.) through Qiagen-tip20 (Qiagen Inc.), elute and precipitate DNA material as recommended by the supplier. Dissolve DNA pellet in 30 $\mu$l of TE buffer, check DNA concentration by EtdBr fluorescence, adjust to 0.1 mg/ml.

e. Ligate 2 $\mu$g of purified Tester DNA amplicon DNA digest to primer set 2, as described above, dilute with TE plus tRNA up to 10 $\mu$g/ml (25 $\mu$g/ml for Hind III representation).

II. DNA Hybridization/Amplification Steps

1. Hybridization 1.

a. Mix 80 $\mu$l of Driver amplicon DNA digest (0.5 mg/ml) and 40 $\mu$l of diluted Tester amplicon ligate (0.4 $\mu$g for representations made with most six cutters, 1 $\mu$g for Hind III representation), extract once with phenol/chloroform.

b. Add 30 $\mu$l of 10 M NH$_4$OAc and 380 $\mu$l (2.5 vol.) of EtOH, chill at –70° C. for 10 min. incubate at 37° C. for 2 min., spin, wash twice with 70% EtOH, dry.

c. Resuspend the pellet in 4 IA of EEx3 buffer (30 mM EPPS from Sigma, pH 8.0 at 20° C., 3 mM EDTA) by vortexing for 2 min., spin the sample to the bottom and overlay with 35 $\mu$l of mineral oil.

d. Denature DNA for 3–4 min. at 98° C. in a heating block, carefully add 1 $\mu$l of 5 M Nacl to the DNA drop and incubate at 67° C. for 20 h.

2. Selective amplification a. Remove oil, add 8 $\mu$l of tRNA solution (5 mg/ml), mix, add 390 $\mu$l of TE buffer and mix again.

b. To fill-in the adapter ends, make 2 tubes with 360 $\mu$l of PCR mix (see above), not including 24-mer primer. Add 40 $\mu$l of hybridized DNA dilution in each tube, place in Thermocycler at 72° C., add 3 $\mu$l of AmpliTaq DNA polymerase, mix, and incubate for 5 min. Add 10 $\mu$l of 24-mer primer (set 2), mix, overlay with mineral oil and perform 10 cycles of PCR as above. For J Bgl 24 primer lower annealing temperature (70° C.) is required.

c. Phenol and phenol/chloroform extract, iProOH ppt. as above, dissolve the pellet in each tube in 20 $\mu$l of dd$H_2O$, combine.

d. Take 20 µl of the amplified difference product 1, add 20 µl of 2×mung bean nuclease buffer and 2 µl of mung bean nuclease (10 U/µl, NEB), incubate at 30° C. for 30 min. Add 160 µl of 50 mM Tris-HCl pH 8.9, inactivate the enzyme by 5 min. incubation at 98° C. Prepare 2 tubes with a PCR mix (360 µl), containing J 24-mer primer, add 40 µl of MBN-treated difference product in each tube and make PCR for 15 cycles as above.

e. Run 10 µl of the amplificate on a 2% agarose gel, estimate the quantity of DNA (usually 0.1–0.3 µg) and, if necessary to improve the yield, make 2–4 additional cycles after addition of 3 µl of fresh AmpliTaq DNA polymerase.

3. Change of adapter on a difference product a. Extract with phenol and phenol/chloroform, iProOH ppt. as above and dissolve the pellet at approx. 0.1 mg/ml. Determine DNA concentration by EtdBr fluorescence, adjust up to 0.1 mg/ml.

b. Digest difference product with chosen restriction enzyme (10 U/µg), extract as above and EtOH ppt., wash, dry, dissolve at 20 ng/µl.

c. Take 10 µl (200 ng) of DNA solution and directly ligate to adapter 3 (primer set 3) in a volume 60 µl as described above. Dilute the ligated difference product up to 1.25 ng/µl (2.5 ng/µl for Hind III representation) with 100 µl of TE buffer containing tRNA (20 µl for Hind III).

4. Subsequent hybridization/amplification steps a. For second hybridization mix 40 µl (50 ng) of adapter ligated difference product (100 ng for Hind III representation) and 80 µl (40 µg) of Driver amplicon DNA digest. Proceed through hybridization/amplification step as above.

b. For third hybridization/amplification step take 100 pg of difference product 2 ligated to the adapter 2 (400 pg for Hind III representation), making final amplification after MBN treatment for 20 cycles (25 for Hind III representation).

c. For Hind III representation sometimes the fourth hybridization/amplification step is needed. Take 5 pg of difference product 3 ligated to adapter 3 with final amplification for 27 cycles.

III. Cloning and Analysis of Difference Products

1. Cloning a. Take 10 µg of the difference product after the last hybridization/amplification step, digest with chosen restriction enzyme, extract with phenol and phenol/chloroform, EtOH ppt.

b. Dissolve obtained DNA in 100 µl of TAE buffer and make 2% low melting point (LMP) gel electrophoresis and DNA purification as above.

c. Dissolve digested difference product in 30 µl of TE buffer, check the concentration and dilute an aliquot (2–5 µg) up to 10 ng/ml with tRNA containing TE buffer.

d. To ligate the difference product in a plasmid vector mix:
  1 µl of 10×ligase buffer,
  6 µl of ddH$_2$O,
  1 µl (10 ng) of gel-purified difference product DNA digest,
  1 µl (40 ng) of any pUC-derived vector, digested with chosen restriction enzyme and dephosphorylated,
  1 µl (400 U) of T4 DNA ligase.
  Incubate for 1–3 h at 16° C. and dilute by addition of 70 µl of tRNA containing TE.

e. Transform the competent DH 5α cells in a standard way. Plate on LB agar containing ampicillin, X-Gal, and IPTG.

2. PCR amplification of cloned inserts a. Prepare PCR tubes each containing 100 µl of standard PCR mixture and sequencing and reverse sequencing primers (seq. 24 and rev. 25, respectively, see Table) (500 pmol of each per tube).

b. Pick and transfer one white bacterial colony in each tube, vortex and place in Thermocycler at 95° C. for 5 min.

c. Lower the temperature by switching to 72° C., add 1 µl (5 U) of AmpliTaq polymerase, mix, overlay with mineral oil and perform PCR for 30 cycles (1 min. at 95° C., 3 min. at 72° C.) with final extension at 72° C. for 10 min.

d. Analyze the yield and the size of the amplified fragments by 2% get electrophoresis of 5 µl aliquots. Purify chosen DNA fragments by Qiagen-tip20 chromatography, iProOH ppt., wash, dry and dissolve in 30 µl of TE.

e. Determine DNA concentration by EtdBr fluorescence. For blot hybridizations dilute 1–2 µg of each fragment up to 10 µg/ml with tRNA containing TE buffer.

EXAMPLE 3

Application of RDA to Isolating DNA Probes That Detect Gene Amplification in Cancers.

When tumor DNA was taken as tester and normal DNA from humans was taken as driver, RDA yielded difference products that hybridized to amplified sequences in the tumor DNA. This is an unanticipated result, the probable consequence of the kinetic enrichment during RDA. Probes that detect amplified sequences in human cancers are of clinical value, since the presence of such sequences usually indicates a poor prognosis. For example, amplification of N-myc or the NEU oncogenes indicates poor prognosis for neuroblastoma or breast cancer, respectively.

Difference products were found when DNA from a melanoma cell line or DNA from a small cell lung cancer cell line was used as tester and normal DNA from the individual donors, respectively, was used as driver. The difference products for the 1st, 2nd and 3rd round subtractions of the melanoma were subject to electrophoretic separation, and are shown in FIG. 1, right hand panel, lanes a, c and e. The difference products for the 1st, 2nd and 3rd rounds of subtractions of the lung cancer are shown in lanes b, d and f. Size markers are in lane g, with lengths in basepairs indicated at right. The melanoma cell line was AH-Mel, and the small cell carcinoma cell line was H1770. When some of the difference products were used as nucleic acid hybridization probes in genomic blots of restriction endonuclease cleaved human DNA from a variety of cancer cell lines, they detected sequences amplified in the small cell carcinoma cell line (top panel, left side of FIG. 1) or the melanoma cell line (middle and lower panel, left side of FIG. 1). The probes derived from the RDA analysis of the small cell carcinoma cell line also detect amplified sequences in a neuroblastoma cell line IMR-5 (top panel, left side). The RDA probes were determined to map to human chromosome 2 (small cell lung carcinoma) and chromosome 3 (melanoma) by hybridizing them to a panel of monochromosomal hybrid cells #2 obtained from NIGMS Human Genetic Mutant Cell Repository. No amplifications on chromosome 3 have been previously described.

Figure 2:
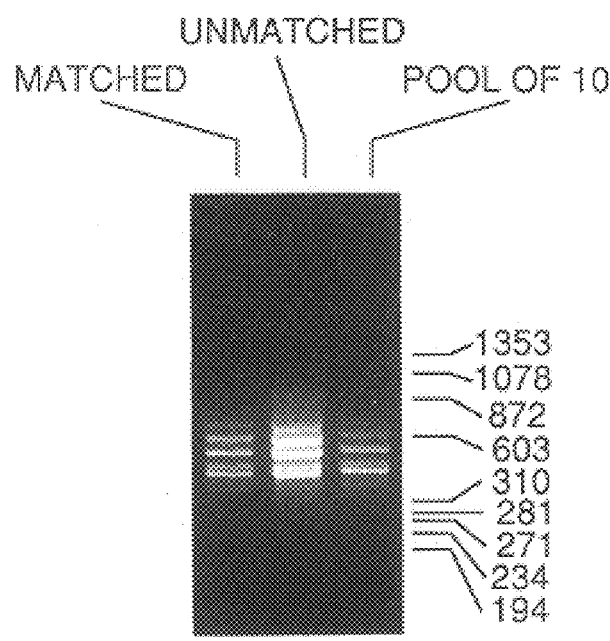
FIG. 2 is a gel electrophoresis analysis of gene amplification using drivers from different sources.

Next, was determined that driver DNA need not derive from the same individual as the tester. RDA was performed using DNA from the melanoma cell line as tester and using DNA from either the matched individual donor, an unmatched individual, or a pool of 10 unmatched individuals as driver. The same pattern of difference products was found whichever driver DNA was used (see FIG. 2). Thus tester and driver DNAs do not have to derive from the same individual when one is searching for probes that detect amplified DNA present in the tester.

EXAMPLE 4
The Use of RDA to Discover New Viruses.

Human prostate cancer biopsies were analyzed using RDA. DNA extracted from a surgical biopsy of a prostate cancer was used as tester and DNA from normal tissue of the same individual was used as driver. A single difference product was obtained and sequenced. Computer analysis demonstrated that this difference sequence corresponded most closely to a rat LINE element, a member of repeated sequences found interspersed throughout the rat genome (see FIG. 3 for a sequence comparison). Oligonucleotide PCR primers derived from the extreme left hand and right hand sequences of this element were used to demonstrate its presence in various DNAs. Its presence was detected in rat DNA, and two different regions of the human prostate cancer, but not in the DNA from normal tissues of the human in which the cancer arose. Thus genetic information from rats has been found in human tissue, presumably through the agency of a virus. The DNA sequences of this presumed virus may be obtained by "chromosomal walking" from the inserted element. One may infer a causal role of this virus in the etiology of this cancer.

EXAMPLE 5
The Use of RDA to Isolate Probes That Detect Genetic Lesions in Cancer.

Using DNA from pure or nearly pure (>90%) cancer cells as tester and DNA from normal cells of the respective patient as driver many difference products were obtained. These difference products detected either loss-of-heterozygosity, hemizygous loss on chromosome Y, or homozygous loss in the tumor DNAs. The probes from RDA were mapped to human chromosomes. The results are summarized in Table 3. As tester, DNAs from four different renal cell carcinoma cell lines UOK114, UOK124, UOK132 and UOK112 were used, and one esophageal cancer biopsy, from patient #758. One probe, RCC124.1 (footnote d from Table 3) also detected homozygous loss on chromosome 2 in one additional renal cancer cell line and two bladder cancer cell lines. One probe, RCC132.12 (footnote e from Table 3) also detected homozygous loss on chromosome 9 in two melanomas. One probe, BAR.6 (footnote f from Table 3) also detects homozygous loss on chromosome 3 from several colon cancer cell lines. Probes that detect homozygous loss may be useful to define loci that encode tumor suppressor genes. Methods that detect loss of function of tumor suppressor genes may be useful in the clinical typing of cancers.

TABLE 3

Application of RDA to the pairs of normal and tumor DNA's (tumor DNA as Driver).

| | RDA fragments | | |
| --- | --- | --- | --- |
| Experiment | Selected for initial characterization[a] | Found to be informative[b] | Chromosomes affected[c] |
| 1. Renal cell carcinoma, cell line UOK114 (male) | 12 | 4 (1/3/0) | 3/3, 3, 10 |
| 2. Renal cell carcinoma, cell line UOK124 (female) | 11 | 5 (2/3/0) | 2[d]/ND |
| 3. Renal cell carcinoma, cell line UOK132 (male) | 10 | 9 (0/3/6) | –/9[e], 9, 5 |
| 4. Renal cell carcinoma, cell line UOK112 (male) | 13 | 13 (0/0/13) | –/– |
| 5. Barrett's esophageal cancer, patient #758, sorted nuclei (male) | 5 | 5 (1/0/4) | 3[f]/– |
| Total | 38 | 23 (4/9/10) | |

[a]Clones with distinct insert sizes.
[b]Entries in parentheses (x/y/z) show distribution of fragments according to type of loss, where x is number of probes detecting homozygous loss, y the number detecting loss of heterozygosity, and z the number detecting hemizygous loss from the Y chromosome.
[c]Chromosomal location of probes, where x/. . . are the locations of probes detecting homozygous loss, and . . ./x the locations of probes detecting loss of heterozygosity. ND means not yet determined.
[d]Probe RCC124.1 also detects homozygous loss in bladder cancer cell lines.
[e]One probe, RCC132.12, detected homozygous loss on chromosome 9 in melanomas.
[f]Probe BAR.6 also detects homozygous loss in four out of seven colon cancer cell lines and one bladder carcinoma cell line.

EXAMPLE 6
The Application of RDA to the Analysis of DNA From Pools of Individual.

RDA may be applied to the discovery of polymorphisms that are genetically linked to an inherited trait such as a disease susceptibility or a behavioral abnormality in humans. To utilize RDA for this purpose, it is desirable to use pools of DNAs from a group of individuals for use as either tester, driver or both. When used this way, RDA may yield probes that detect polymorphic alleles that are present in one group and not in another. In particular, when such pools are used as driver, RDA yields probes for restriction endonuclease polymorphisms (PARFs) that distinguish tester from all individuals in the driver pool. When pools are used as tester, RDA yields PARFs that distinguish at least one member of the tester pool from the driver individual. In the most challenging example, when both tester and driver are pooled DNAs from groups of individuals, RDA yields PARFs that distinguish at least one member of the tester group from all members of the driver group.

This is illustrated in Table 4. Two groups of humans were taken: ten that shared a genetic abnormality, neuronal ceroid lipo-fuscinosis, also known as Batten's disease, and ten that did not have this condition. DNAs were prepared from cells of each individual and pooled accordingly. Pools of DNA were used for RDA using DNA from one group as tester and DNA from the other as driver, and then reversing the procedure. In each case difference products were obtained that detected PARFs. In Table 4 the probe name is listed, and "+" indicates that it detected the small allele of the PARF in a given individual. As the Table shows, when normal individuals were used as tester, probes (pA1, pA2, pA4, and pA9) were obtained that detected small PARF alleles in at least one member of the group, and this allele was always absent in the individuals with Batten's disease. Similarly, when DNAs from the affected group was used as tester, probes (pN2, pN7, pN9, pN13 and pN15) were obtained that detected small PARF alleles in at least one member of the affected group, and this allele was always absent in the normal group.

TABLE 4

Screening for presence of Bgl II PARF's in 20 human DNA amplicons

| | Affecteds | | | | | | | | | | Normals | | | | | | | | | | Length of small |
|---|---|---|---|---|---|---|---|---|---|---|---|---|---|---|---|---|---|---|---|---|---|
| Probe | 1 | 2 | 3 | 4 | 5 | 6 | 7 | 8 | 9 | 10 | 1 | 2 | 3 | 4 | 5 | 6 | 7 | 8 | 9 | 10 | allele (bp) |
| pA1 | | | | | | | | | | | | | | | + | + | | | + | | 300 |
| pA2 | | | | | | | | | | | | | | + | + | | | + | + | + | 120 |
| pA4 | | | | | | | | | | | | | | + | | | | | | | 150 |
| pA9 | | | | | | | | | | | | | | | + | + | | | | + | 400 |
| pN2 | | | | | | | | | | + | | | | | | | | | | | 425 |
| pN7 | + | + | + | | + | | | | | + | | | | | | | | | | | 300 |
| pN9 | | | | | | | | | | + | | | | | | | | | | | 350 |
| pN13 | | | + | + | + | | | | | | | | | | | | | | | | 400 |
| pN15 | | | | | | | | | | + | | | | | | | | | | | 600 |

EXAMPLE 7
The Use of RDA in Obtaining Probes That Reflect Differences in RNA Populations.

RDA can be applied to compare populations of double stranded cDNAs derived from RNA. The difference products will yield probes that detect sequences expressed among the RNA from one source that are not equivalently expressed in another. Such probes are sometimes of use in diagnosis (e.g. to determine the origin of a cell, or to find evidence of infection) and can lead to the discovery of important tissue-specific or disease related genes.

Figure 4:
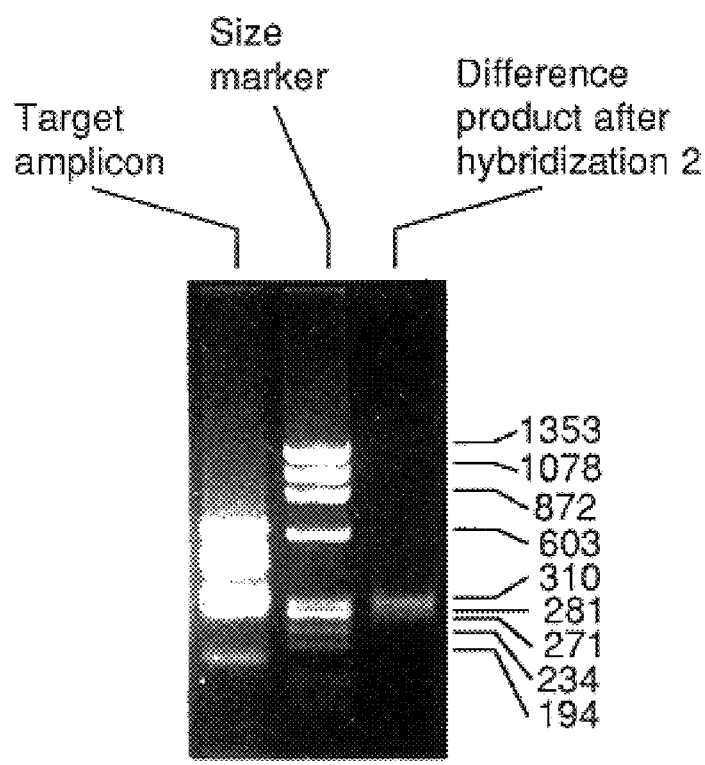
FIG. 4 is a gel electrophoresis analysis of difference sequences between two cDNA populations.

A double stranded cDNA population was prepared from RNA extracted from a male mouse brain. This was used as driver. A one hundred thousandth part of double stranded DNA from the kanamycin resistance gene encoded by an *E. coli* plasmid was added to a small portion of this cDNA, and this used as tester. This model system mimics the case of a single small difference between the expressed RNAs from two sources. RDA was performed on these two samples using the enzyme Sau3A to prepare the respective amplicons. The difference product after two rounds of substraction was separated using gel electrophoresis, as shown in FIG. 4. In the left hand lane is shown an electrophoretic separation of amplicons prepared from 1.2 kb of the kanamycin gene. In the middle lane were size markers. The difference product from the RDA is seen in the right hand lane. This product was derived from the kanamycin gene as shown by blot hybridization, thus proving that RDA can be used to detect differences in DNAs derived from RNA populations.

It is evident from the above results, that a powerful tool has been provided for isolating probes which can be used to identify sequence differences between two related genomes. This technique may be used in a wide variety of contexts in relation to forensic medicine, detecting the presence of pathogenic DNA, lesions occurring in neoplastic cells, genetic counseling, the presence of genes associated with genetic diseases, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A kit comprising:

at least two probes prepared according to a method for producing probes capable of distinguishing at least one sequence difference between genomes from a neoplastic cell source and a related normal cell source, said method comprising completely digesting separately the DNA from said genomes from said neoplastic cell source and said related normal cell source with a restriction endonuclease to produce first and second digested fragments respectively, wherein DNA from said normal cell source is driver DNA, and DNA from said neoplastic cell source is tester DNA, wherein said tester DNA comprises target DNA, wherein said target DNA comprises sequence differences between said genomes of said neoplastic cell source and said related normal cell source comprising at least one of an insertion, deletion, rearrangement or DNA amplification defining target DNA;

ligating a first set of adaptors to said first and second digested fragments and amplifying said first and second fragments using primers to one of the strands of said first set of adaptors to provide amplified amounts of said first and second fragments of said digested sequences of less than about 2 kbp as first and second amplicons, respectively;

carrying out a first round of the following steps for enrichment of target DNA:

removing said first set of adaptors from said first and second amplicons and ligating a second set of adaptors to 5' ends of said first amplicon;

combining under melting and annealing conditions said first amplicon with a large excess of said second amplicon, whereby a portion of the resulting dsDNA comprises self-annealed tester DNA including target DNA;

filling in the 3' ends of overhangs;

amplifiing said dsDNA with primers to one of said strands of said second set of adaptors to enrich for target DNA;

repeating said first round of steps for at least 1 additional round, using a different set of adaptors as to the previous round in each successive round to provide a DNA composition comprising a predominant amount of target DNA; and cloning said DNA composition to provide clones having a substantially homogeneous probe of target DNA.

2. A kit comprising:

at least two probes prepared according to a method for producing probes capable of distinguishing at least one sequence difference between genomes from a neoplastic cell source and a related normal cell source, said method comprising completely digesting separately the DNA from said genomes from said neoplastic cell source and a related normal cell source with a restriction endonuclease to produce first and second digestion fragments, wherein DNA from said neoplastic cell source is driver DNA, and DNA from said normal cell source is tester DNA, wherein said tester DNA comprises target DNA, wherein said target DNA comprises sequence differences between said genomes of said neoplastic cell source and said related normal cell source comprising loss of heterozygosity, homozygosity or hemizygous loss to define said target DNA;

ligating a first set of adaptors to said first and second digested fragments and amplifying said first and second fragments using primers to one of the strands of said first set of adaptors to provide amplified amounts of said first and second fragments of said digested sequences of less than about 2 kbp as first and second amplicons, respectively;

carrying out a first round of the following steps for enrichment of target DNA:

removing said first set of adaptors from said first and second amplicons and ligating a second set of adaptors to 5' ends of said second amplicon;

combining under melting and annealing conditions said second amplicon with a large excess of said first amplicon, whereby a portion of the resulting dsDNA comprises self-annealed tester DNA including target DNA;

filling in the 3' ends of overhangs;

amplifying said dsDNA with primers to one of said strands of said second set of adaptors to enrich for target DNA;

repeating said first round of steps for at least 1 round, using a different set of adaptors as to the previous round in each successive round to provide a DNA composition comprising a predominant amount of target DNA; and cloning said DNA composition to provide clones having a substantially homogeneous probe of target DNA.

* * * * *

SEQUENCE LISTING

<160> NUMBER OF SEQ ID NOS: 18

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:
                    OLIGONUCLEOTIDE

<400> SEQUENCE: 1
agcactctcc agcctctcac cgca                                      24

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence:
                    OLIGONUCLEOTIDE

```
<400> SEQUENCE: 2
gatctgcggt ga                                                              12

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
                       OLIGONUCLEOTIDE

<400> SEQUENCE: 3
accgacgtcg actatccatg aaca                                                 24

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence:
                       OLIGONUCLEOTIDE

<400> SEQUENCE: 4
gatctgttca tg                                                              12

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
                       OLIGONUCLEOTIDE

<400> SEQUENCE: 5
aggcaactgt gctatccgag ggaa                                                 24

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence:
                       OLIGONUCLEOTIDE

<400> SEQUENCE: 6
gatcttccct cg                                                              12

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:
                       OLIGONUCLEOTIDE

<400> SEQUENCE: 7
agcactctcc agcctctcac cgag                                                 24

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence:
                       OLIGONUCLEOTIDE

<400> SEQUENCE: 8
```
gatcctcggt ga					12

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
       OLIGONUCLEOTIDE

<400> SEQUENCE: 9
accgacgtcg actatccatg aacg					24

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence:
       OLIGONUCLEOTIDE

<400> SEQUENCE: 10
gatccgttca tg					12

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:
       OLIGONUCLEOTIDE

<400> SEQUENCE: 11
aggcaactgt gctatccgag ggag					24

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence:
       OLIGONUCLEOTIDE

<400> SEQUENCE: 12
gatcctccct cg					12

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence:
       OLIGONUCLEOTIDE

<400> SEQUENCE: 13
agcttgcggt ga					12

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence:
       OLIGONUCLEOTIDE

<400> SEQUENCE: 14

-continued

```
agcttgttca tg                                                   12

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
                       OLIGONUCLEOTIDE

<400> SEQUENCE: 15
aggcagctgt ggtatcgagg gaga                                      24

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence:
                       OLIGONUCLEOTIDE

<400> SEQUENCE: 16
agcttctccc tc                                                   12

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:
                       OLIGONUCLEOTIDE

<400> SEQUENCE: 17
cgacgttgta aaacgacggc cagt                                      24

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:
                       OLIGONUCLEOTIDE

<400> SEQUENCE: 18
cacacaggaa acagctatga ccatg                                     25
```